(12) United States Patent
Douglass et al.

(10) Patent No.: US 9,237,934 B2
(45) Date of Patent: Jan. 19, 2016

(54) SYSTEM FOR STETHOSCOPE HEAD DISINFECTION

(71) Applicant: Scope Swipe, LLC, Sebastian, FL (US)

(72) Inventors: James W. Douglass, Indialantic, FL (US); Pedro Espat, Sebastian, FL (US); Michael Layton, Vero Beach, FL (US); Mary Layton, Vero Beach, FL (US); Eric Petersen, Homestead, FL (US); John S. Scott, Sebastian, FL (US)

(73) Assignee: Scope Swipe, LLC, Sebastian, FL (US)

( * ) Notice: Subject to any disclaimer, the term of this patent is extended or adjusted under 35 U.S.C. 154(b) by 0 days.

(21) Appl. No.: 14/741,417

(22) Filed: Jun. 16, 2015

(65) Prior Publication Data

US 2015/0359600 A1 Dec. 17, 2015

Related U.S. Application Data

(60) Provisional application No. 61/998,003, filed on Jun. 16, 2014.

(51) Int. Cl.
| | |
|---|---|
| *A61B 19/00* | (2006.01) |
| *A61L 2/18* | (2006.01) |
| *A61B 7/02* | (2006.01) |
| *B08B 1/04* | (2006.01) |
| *A61L 2/00* | (2006.01) |

(52) U.S. Cl.
CPC . *A61B 19/34* (2013.01); *A61B 7/02* (2013.01); *A61L 2/18* (2013.01); *A61B 2019/343* (2013.01); *A61L 2/00* (2013.01); *A61L 2202/24* (2013.01); *B08B 1/04* (2013.01)

(58) Field of Classification Search
CPC .... A61B 19/34; A61B 2019/343; B08B 1/00; B08B 1/04; A61L 2/00; A61L 2/18; A61L 2202/24
USPC ............ 15/21.1, 97.1, 97.2, 99; 422/292, 300
See application file for complete search history.

(56) References Cited

U.S. PATENT DOCUMENTS

| | | |
|---|---|---|
| 5,641,464 A | 6/1997 | Briggs, III et al. |
| 5,892,233 A | 4/1999 | Clement |
| 6,018,835 A | 2/2000 | Schonfeld |
| 7,282,177 B2 | 10/2007 | Castaneda |
| 7,360,625 B2 | 4/2008 | Stickley |
| 7,406,973 B1 | 8/2008 | Perlman et al. |
| 7,705,325 B2 | 4/2010 | Vestal |
| 7,942,597 B2 | 5/2011 | Perlman et al. |
| 8,057,117 B2 | 11/2011 | Perlman et al. |
| 8,083,998 B2 | 12/2011 | Hurwitz et al. |
| 8,387,745 B2 | 3/2013 | Gross |
| 8,393,818 B2 | 3/2013 | Perlman et al. |
| 8,403,583 B2 | 3/2013 | Perlman et al. |

(Continued)

*Primary Examiner* — Michael Jennings
(74) *Attorney, Agent, or Firm* — Daniel Pierron; Widerman Malek, PL

(57) ABSTRACT

A stethoscope disinfection system comprising a guide member comprising a body member, a rotation-imparting member, a slide guide track, a spring guide track, and a trolley guide track, and a trolley comprising a lower housing member, a cam member, a lock head, a spring apparatus, a brush member, an upper housing member configured to receive at least a portion of a head of a stethoscope, and a dispersing member positioned in the dispersing mechanism chamber. The system may further comprise a slide guide configured to engage with each of the arm of the lock head and the slide guide track and to translate along a length of the slide guide track.

20 Claims, 8 Drawing Sheets

(56) References Cited

U.S. PATENT DOCUMENTS

| | | | |
|---|---|---|---|
| D685,469 S * | 7/2013 | Cole | D24/134 |
| 8,662,244 B2 | 3/2014 | Fishberger et al. | |
| 8,795,438 B2 * | 8/2014 | Rubin | A61B 19/34 134/56 R |
| 9,056,148 B2 * | 6/2015 | Zawoy | A61B 7/02 |
| 2007/0256753 A1 * | 11/2007 | Riley | A61B 19/34 141/69 |
| 2008/0019889 A1 * | 1/2008 | Rogers | A61B 19/34 422/292 |
| 2009/0020135 A1 * | 1/2009 | Adams | A61L 2/0011 134/1 |
| 2013/0306105 A1 * | 11/2013 | Battah | A61B 19/34 134/6 |
| 2014/0010711 A1 * | 1/2014 | Dam | A61L 2/18 422/28 |

* cited by examiner

SYSTEM FOR STETHOSCOPE HEAD DISINFECTION

RELATED APPLICATIONS

This application claims the benefit under 35 U.S.C. §119 (e) of U.S. Provisional Patent Application Ser. No. 61/998,003 titled System for Stethoscope Head Disinfection, Scrubbing, and Drying Meeting Health Care Provider Operational, Cost, and Space Needs filed Jun. 16, 2015, the content of which is incorporated by reference in its entirety.

FIELD OF THE INVENTION

The present invention relates to systems for cleaning at least a portion of a stethoscope head.

BACKGROUND

The transmission of bacteria as a result of use of stethoscopes without engaging in proper cleaning of the stethoscope is an increasing cause for concern. Previous solutions have included the use of an alcohol swab. However, such solutions are inconvenient for the medical professional using the stethoscope, as it requires them to open a single-use swab, throw the wrapper away, and then manually clean the stethoscope. Moreover, such a solution relies on the thoroughness of the user to perform adequate cleaning.

Other solutions have utilized UC irradiation of the stethoscope. However, such solutions require a power source, which can be inconvenient for the user, either requiring replacement or recharging of batteries, or frequent trips to a device that is located near a power source. Moreover, such solutions require substantial amounts of time to be effective, creating a delay in a field where the time of interaction between the user and the patient is increasingly diminished Yet other solutions have relied on a disinfecting spray, but do not provide for the mechanical cleaning of the stethoscope. As such, a biofilm may accumulate on the surface of the stethoscope, both reducing the effectiveness of the spray and negatively affecting the performance of the stethoscope.

Accordingly, there is a need in the art for a solution in the art to provide for a quick, reliable, and effective device for cleaning a stethoscope head.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a stethoscope disinfection system comprising, a guide member, the guide member comprising a body member, a rotation-imparting member, a slide guide track and a spring guide track. The guide member may further comprise a trolley guide track. The system may further comprise a trolley configured to removably attach to the guide member. The trolley may comprise a lower housing member that may be configured to engage with the trolley guide track and a cam member that may be configured to engage with the rotation-imparting member to have motion imparted to the cam member thereby. The cam member may comprise a dispersing mechanism chamber. Additionally, the trolley may further comprise a lock head comprising an arm and a spring apparatus that may be configured to engage with each of the spring guide track and the arm of the lock head. The spring apparatus may be configured to transition between an expanded state and a compressed state. The trolley may further comprise a brush member positioned generally above the cam member and that may be attached to the spring apparatus, an upper housing member that may be configured to receive at least a portion of a head of a stethoscope, and a dispersing member positioned in the dispersing mechanism chamber. The system may further comprise a slide guide that may be configured to engage with each of the arm of the lock head and the slide guide track and to translate along a length of the slide guide track.

The dispersing member may be configured to be actuated by the rotation of the cam member to disperse a disinfectant solution. Additionally, the spring apparatus may be configured to transition from the expanded state to the compressed state when translating in a distal direction. Furthermore, the spring apparatus may be configured to transition from the compressed state to the expanded state upon the slide guide disengaging with the arm of the lock head. The brush member may be translated vertically by the transition of the spring apparatus from the compressed state to the expanded state. Additionally, the transition of the trolley in a proximal direction may cause the brush member to be rotated. Furthermore, the slide guide may be configured to engage with the arm of the lock head when the trolley is translated in a proximal direction to a proximal end of the trolley guide track and the slide guide is translated in a proximal direction to a proximal end of the slide guide track.

In some embodiments, the rotation-imparting member comprises a plurality of teeth. Furthermore, the body member of the guide member may comprise an upper surface including a recess formed therein, and the plurality of teeth may extend into the recess and are positioned along a length of the recess. Additionally, the cam member may further comprise a rotation section configured to engage with the plurality of teeth and have rotation imparted to the cam member thereby.

In some embodiments, the spring guide track may comprise a proximal section, a distal section, and a transition section. Additionally, the spring apparatus may be configured to be in the expanded state when engaged with the proximal section of the spring guide track. Furthermore, the spring apparatus may be configured to transition to the compressed state when translating through the transition section in a distal direction. The spring apparatus may be configured to remain in the expanded state when translating through the transition section in a proximal direction.

In some embodiments, the spring apparatus may be configured to be at a first election when engaged with the proximal section of the spring guide track, to transition to a second elevation when translating through the transition section in a distal direction, and to transition from the second elevation to the first elevation when translating through the transition section in a proximal direction.

In some embodiments, the lower housing member may comprise a body portion that may comprise an exterior wall and an interior wall and a pair of guide sections that may be configured to engage with the trolley guide track. The interior wall may comprise an eccentric portion. Furthermore, the cam member may further comprise a depressible arm. Additionally, the dispersing member may comprise a reservoir configured to contain a disinfectant solution, and a pump-action spray head positioned in fluidic communication with the reservoir. The depressible arm may be configured to interface with and be deflected by the inner wall of the lower housing member when the cam member is rotated. Furthermore, the deflection of the depressible arm may be configured to actuate the pump-action spray head. Additionally, the pump-action spray head may be configured to disperse disinfectant solution from the reservoir when actuated by the depressible arm while rotating as a result of the rotation of the cam member.

In some embodiments, the brush member may further comprise a brush surface, a body member, and an aperture configured to permit the dispersion of fluid therethrough. In some embodiments, the upper housing member may comprise a sidewall, an upper wall, a stethoscope aperture formed in at least one of the sidewall and the upper wall that may be configured to receive at least a portion of a head of a stethoscope, a cavity defined by each of the sidewall and the upper wall, and/or an opening at a lower end of the upper housing member.

In some embodiments, at least one of the guide member and the trolley comprises a cycle counter configured to count the number of cycles the trolley performs. Additionally, the guide member may be configured to be attached to a surface of an external structure.

In some embodiments, the guide member may further comprise a tang. The tang may be configured to prevent the detachment of the trolley from the guide member when in an undeflected state. Additionally, the tang may be configured to permit the attachment or detachment of the trolley to the guide member when in a deflected state.

DETAILED DESCRIPTION OF THE INVENTION

Figure 1:
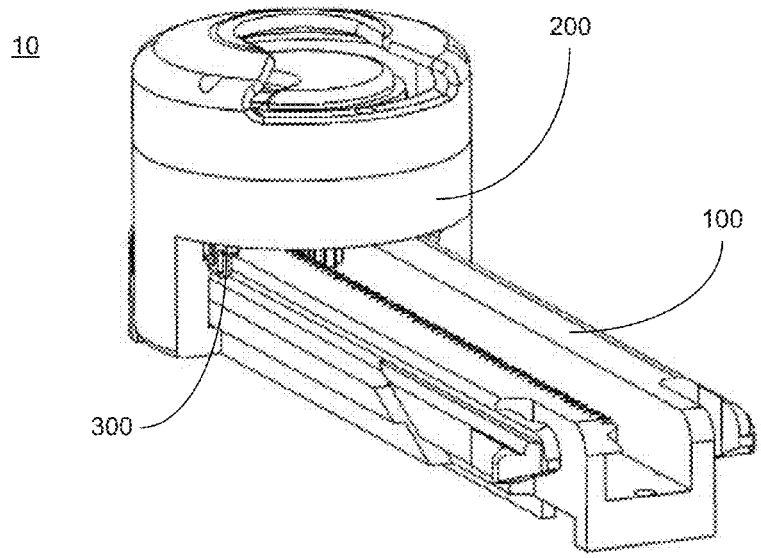
FIG. 1 is a perspective view of a stethoscope disinfection system according to an embodiment of the present invention.
Figure 2:
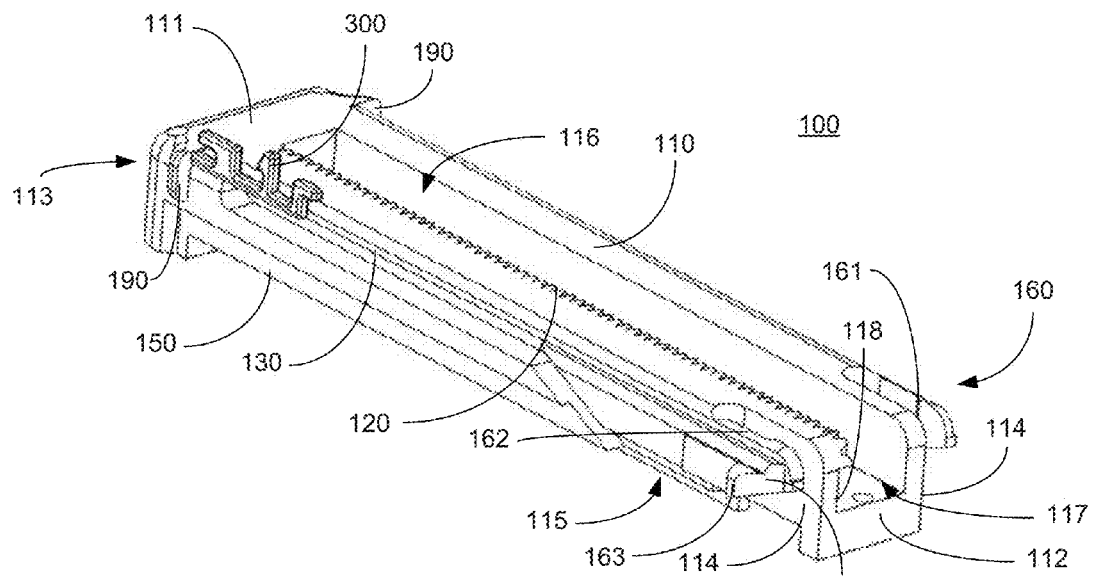
FIG. 2 is a perspective view of a guide member and a slide guide of the stethoscope disinfection system of FIG. 1.
Figure 3:
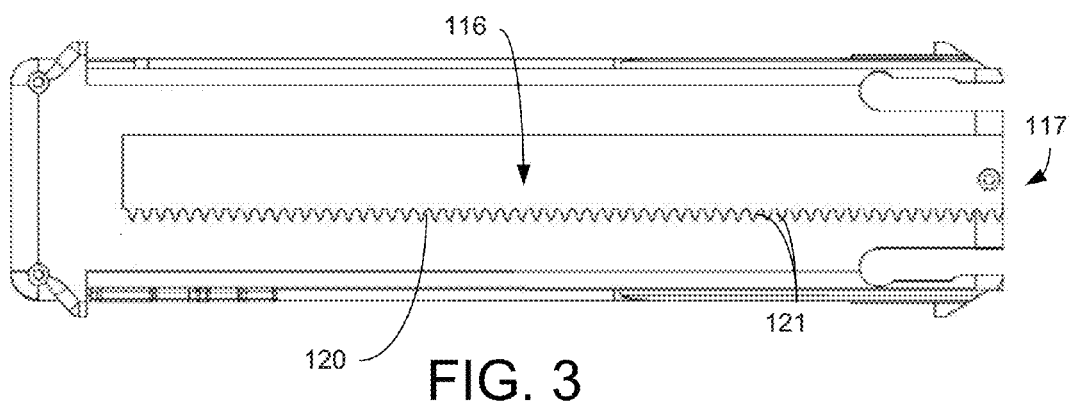
FIG. 3 is a top plan view of the guide member and the slide guide of the stethoscope disinfection system of FIG. 1.
Figure 4:
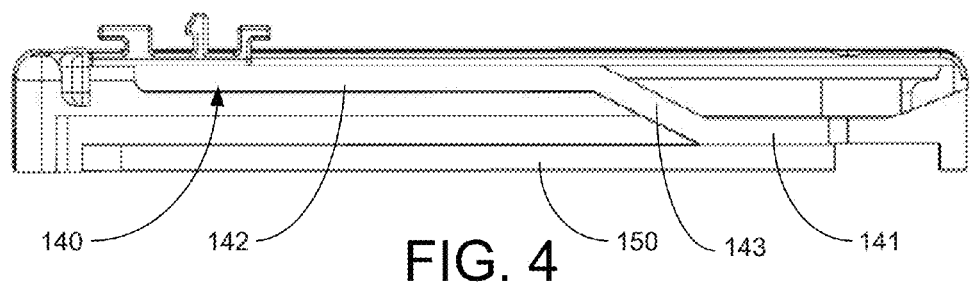
FIG. 4 is a side elevation view of the guide member and the slide guide of the stethoscope disinfection system of FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a system for stethoscope disinfection. The stethoscope disinfection system may be configured to facilitate the cleaning of a portion of a stethoscope head, such as the bell, diaphragm, or other structure. More specifically, the system may enable the cleaning of a portion of the stethoscope head by enabling the portion to be placed inside a trolley of the system, and then translating the trolley to a distal end of the system, and then back to a proximal end, at which time the portion of the stethoscope head placed within the trolley will be clean.

Referring now to FIGS. 1-15, a stethoscope disinfection system 10 will now be discussed in detail. The system 10 may comprise a guide member 100, a trolley 200, and a slide guide 300. The trolley 200 may be configured to be removably attachable to each of the guide member 100 and the slide guide 300, so as to translate along a length of the guide member 200 and be actuated by such translation, thereby causing a portion of a stethoscope positioned therewithin to be cleaned.

Referring now specifically to FIGS. 2-6, the guide member 100 will now be discussed in greater detail. The guide member 100 may be configured to permit the trolley 200 to be removably attachable thereto. Additionally, the guide member 100 may be configured to cause a portion of the trolley 200 to be actuated when the trolley 200 is translated along a length of the guide member 100. More specifically, when the trolley 200 is translated along or parallel to a longitudinal axis of the guide member 100, in either a distal direction or a proximal direction, the guide member 100 may include one or more structures or features configured to cause an element of the trolley 200 to be actuated, thereby enabling the trolley 200 to clean at least a portion of a stethoscope head associated with the trolley 200.

The guide member 100 may comprise a body member 110. The body member 110 may define the longitudinal axis of the guide member 100 and comprise the material within which many features of the guide member 100 may be formed. The body member 110 may comprise an upper surface 111, a proximal end wall 112, a distal end wall 113, opposing sidewalls 114, and a lower wall 115.

The upper surface 111 may comprise a recess 116. The recess 116 may be formed along the substantial length of the guide member 100. The recess 116 may be configured to permit a portion of the trolley 200 to be positioned therewithin. Furthermore, the recess 116 may be configured to permit a portion of the trolley 200 to translate through the length of the recess 116.

The proximal end wall 112 may have formed therein a proximal aperture 117. The proximal aperture 117 may be configured to cooperate with the recess 116 so as to enable a portion of the trolley 200 to pass through the proximal aperture 117 and into the recess 116. This may facilitate the removable attachment of the trolley 200 to the guide member 100.

The guide member 100 may comprise a rotation-imparting member 120. The rotation imparting-member 120 may be configured to interface, engage, or otherwise interact with a structure of the trolley 200 to impart rotational motion to a part of the trolley 200. In this way, the interaction between the rotation-imparting member 120 and the trolley 200 may actuate an element of the trolley 200 so as to perform a cleaning of a stethoscope associated with the trolley 200.

The rotation-imparting member 120 may be any structure or device that may cause the rotation of a part of the trolley 200. In the present embodiment, the rotation-imparting member 120 comprises a plurality of teeth 121. The plurality of teeth 121 may be positioned so as to extend into the recess 116. Additionally, the plurality of teeth 121 may be positioned along the length of the recess 116. More specifically, the plurality of teeth 121 may extend into the recess 116 from a sidewall 118 that partially defines the recess 116. Furthermore, the plurality of teeth 121 may extend inward into the recess 116 from an upper section of the sidewall 118. In some embodiments, the plurality of teeth 121 may be integrally formed with the body member 110.

The guide member 100 may further comprise a slide guide track 130. The slide guide track 130 may be configured to facilitate the engagement of the slide guide 300 to the guide member 100. Additionally, the slide guide track 130 may be configured to limit the distance the slide guide 300 may translate along the length of the guide member 100 in proximal and distal directions. More specifically, the slide guide track 130 may be configured to have a length that causes the trolley 200 and the slide guide 300 to translate different distances proximally and distally relative to the guide member 100. This difference in translatable differences between the trolley 200 and the slide member 300 may facilitate the attachment and detachment of the slide member 300 and one or more structures of the trolley 200, as will be discussed in greater detail hereinbelow.

The slide guide track 130 may be formed in the body member 110. More specifically, the slide guide track 130 may be formed towards an outer edge of the upper surface 111 and/or towards an upper edge of a sidewall 114. Additionally, the slide guide track 130 may be configured to facilitate the slide guide 300 to engage therewith, and be dimensioned such that when the slide guide 300 is engaged therewith, extends upward and above the upper surface 111. In some embodiments, a plurality of slide guide tracks 130 may be comprised by the guide member 100. For example, an identical slide guide track 130 may be formed in the sidewall 114 that opposes the sidewall 114 in which the slide guide track 130 of the depicted embodiment is formed within.

The guide member 100 may further comprise a spring guide track 140. The spring guide track 140 may be configured to facilitate the engagement of a spring apparatus comprised by the trolley 200 therewith, as will be discussed in greater detail hereinbelow. Furthermore, the spring guide track 140 may be configured to permit the spring apparatus to translate along a length of the spring guide track 140. Additionally, the spring guide track 140 may be configured to alter the position of the attached spring apparatus as the spring apparatus translates in proximal and distal directions along the length thereof.

Figure 5:
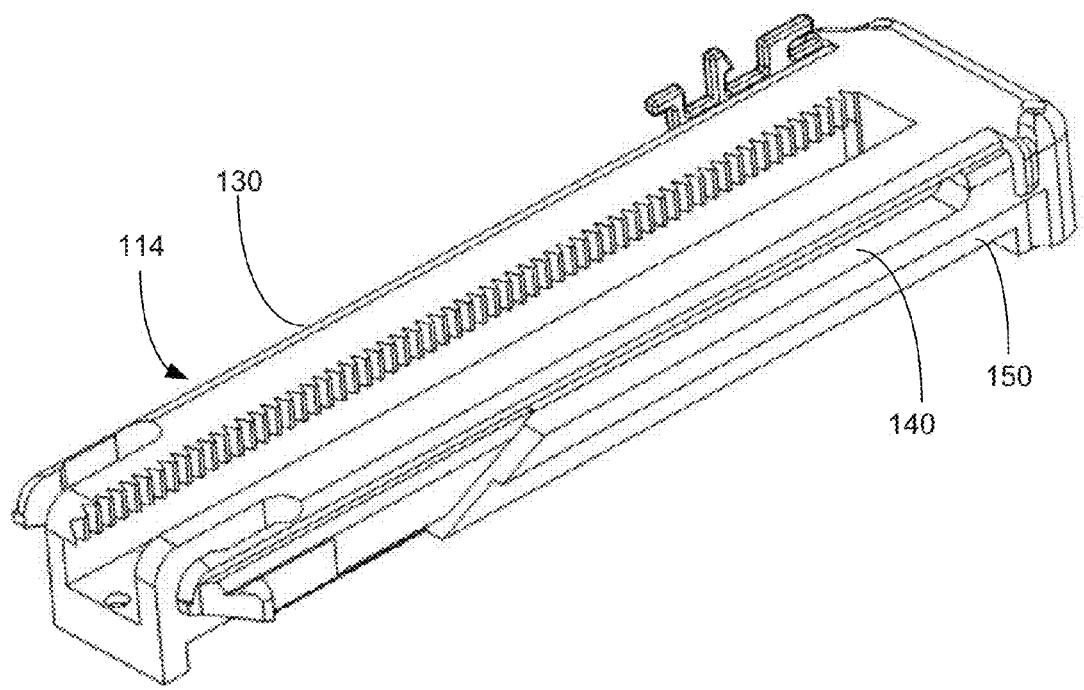
FIG. 5 is a perspective view of the guide member and the slide guide of the stethoscope disinfection system of FIG. 1.

The spring guide track 140 may be formed in any part of the body member 110. In the present embodiment, the spring guide track 140 is formed in a sidewall 114 of the body member 110. More specifically, the spring guide track 140 may be formed generally lower than the slide guide track 130, where the slide guide track 130 and the spring guide track 140 are formed in the same sidewall 114. As can be seen in FIG. 5, the spring guide track 140 may be formed in a sidewall 114 generally opposite the sidewall 114 the slide guide track 130 is formed in. Furthermore, in some embodiments, the guide member 100 may comprise two or more spring guide tracks 140. The spring guide tracks 140 may, in some embodiments, be formed in each of the opposing sidewalls 114, and may each enable separate spring apparatuses to engage therewith.

In some embodiments, the spring guide track 140 may be segmented. The segmentation of the spring guide track 140 may be delineated according to the effect each segment or section has on the attached spring apparatus as it translates along the length of the spring guide track 140. In the present embodiment, the spring guide track 140 may comprise a proximal section 141, a distal section 142, and a transition section 143. The proximal section 141 may be configured to cause the attached spring apparatus to be in a first position, the distal section 142 may be configured to cause the attached spring apparatus to be in a second position, and the transition section 143 may be configured to cause the attached spring apparatus to transition between the first and second positions. More specifically, the transition section 143 may be configured to cause the attached spring apparatus to transition from the first to the second position when the spring apparatus travels in a distal direction along the spring guide track 140, and from the second to the first position when the spring apparatus travels in a proximal direction along the spring guide track 140.

The spring guide track 140 may be configured to have a length so as to permit the various other tracks of the guide member 100, including the spring guide track 130 as described hereinabove, and a trolley guide track, as will be described in detail hereinbelow, to permit the attached structures of the stethoscope disinfection system 10 to translate along lengths thereof at distances and to positions as is required for the successful operation of the stethoscope disinfection system 10.

In the present embodiment, the proximal section 141 may be formed in the sidewall 114 at a position generally lower than the distal section 142, and the transition section 143 may be generally angled so as to connect a distal end of the proximal section 141 with a proximal end of the distal section 142.

The guide member 100 may further comprise a trolley guide track 150. The trolley guide track 150 may be configured to facilitate the attachment of the trolley 200 to the guide member 100, and to enable the trolley 200 to translate along the length of the guide member 100. More specifically, the trolley guide track 150 may be configured to engage or interface with a structure of the trolley 200 so as to permit the engaged structure to slide along the length of the trolley guide track 150.

The trolley guide track 150 may be formed in one or both of the sidewalls 114 of the body member 110. Furthermore, the trolley guide track 150 may be formed toward a lower edge of the sidewalls 114. This may be advantageous in maintaining the proper orientation of the trolley 200 respective to the guide member 100, prevent the trolley 200 from tipping, twisting, or otherwise being positioned in an undesirous orientation.

In some embodiments, one or more of the slide guide track 130, the spring guide track 140, and the trolley guide track 150 may overlap or generally occupy the same space. In such embodiments, each of the respective tracks may be configured so as to enable the successful translation of the attached structure through the overlapping section while no inhibiting the translation of the attached structure associated with the overlapped track. In the present embodiment, the spring guide track 140 and the trolley guide track 150 may occupy the same space in the sidewall 114.

In some embodiments, the guide member 100 may comprise one or more trolley retention members 160. The trolley retention members 160 may be configured to prevent or otherwise inhibit the detachment of the trolley 200 when attached to the guide member 100. Additionally, the trolley retention members 160 may be configured to be actuated, adjusted, or otherwise manipulated so as to permit the trolley 200 to be detached from guide member 100. Any type of retention member as is known in the art is contemplated and included within the scope of the invention, including, but not limited to, catches, hooks, latches, magnetic attachment devices, electromagnet attachment devices, clasps, eye-and-loop structures, snaps, other detachable fasteners, and the like.

In the present embodiment, the trolley retention members 160 may comprise a plurality of tangs 161. The plurality of tangs 161 may extend generally proximally and may be integrally formed with the body member 110. In some embodiments, the plurality of tangs 161 may be discretely formed and attached to the guide member 100. The plurality of tangs 161 may comprise a deflectable arm 162. The deflectable arm 162 may be configured to be deflected inward by manipulation by a user. As such, there may be a gap between the deflectable arm 162 and any other structure of the guide member 100. Additionally, the plurality of tangs 161 may further comprise an outcropping 163 extending generally outwardly from a proximal end of the deflectable arm 162. The outcropping 163 may be configured to engage with a structure of the trolley 200, when the deflectable arm 162 is in an undeflected state, so as to prevent or otherwise inhibit the detachment of the trolley 200 from the guide member 100. Additionally, the outcropping 162 may be configured such that when the deflectable arm 162 is in a deflected state, the outcropping 163 may disengage from the trolley 200 and permit the trolley 200 to detach from the guide member 100 by translating beyond the proximal end of the guide member 100.

Additionally, the guide member 100 may comprise one or more stops 190. The stops 190 may be configured to prevent the distal translation of one or more structures of the system 10, including, but not limited to, the trolley 200 and the slide guide 300. In the present embodiment, the stops 190 are integrally formed outcroppings extending generally outwardly from the sidewalls 114.

Figure 6:
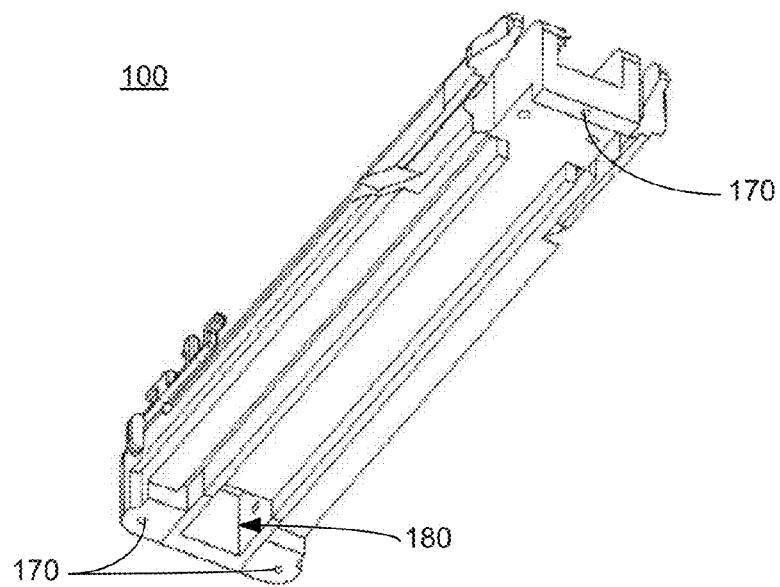
FIG. 6 is a lower perspective view of the guide member and the slide guide of the stethoscope disinfection system of FIG. 1.
Figure 7:
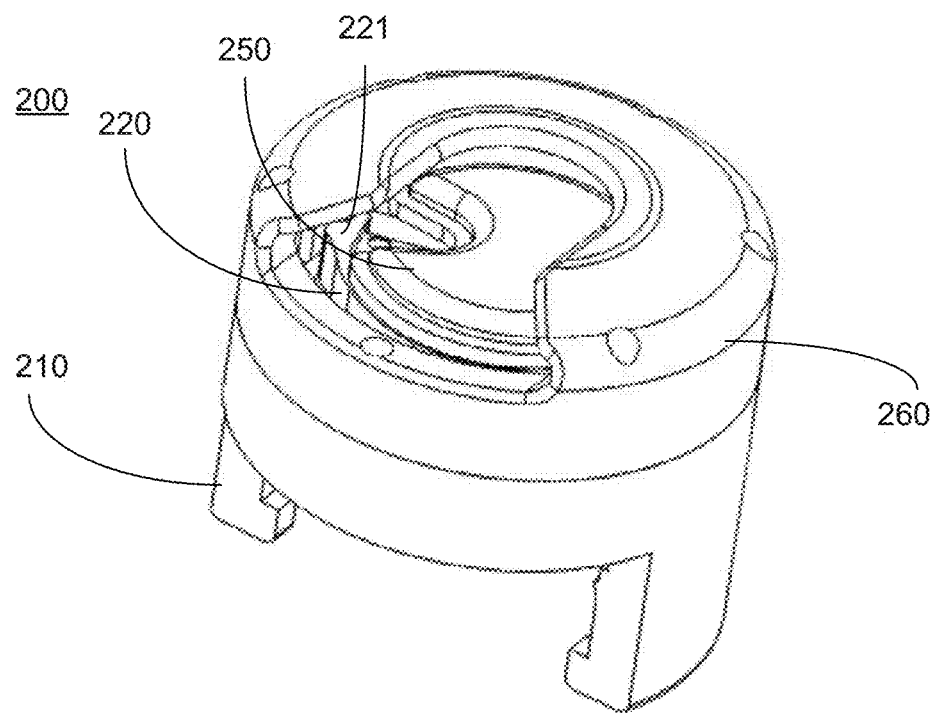
FIG. 7 is a perspective view of the trolley of the stethoscope disinfection system of FIG. 1.
Figure 8:
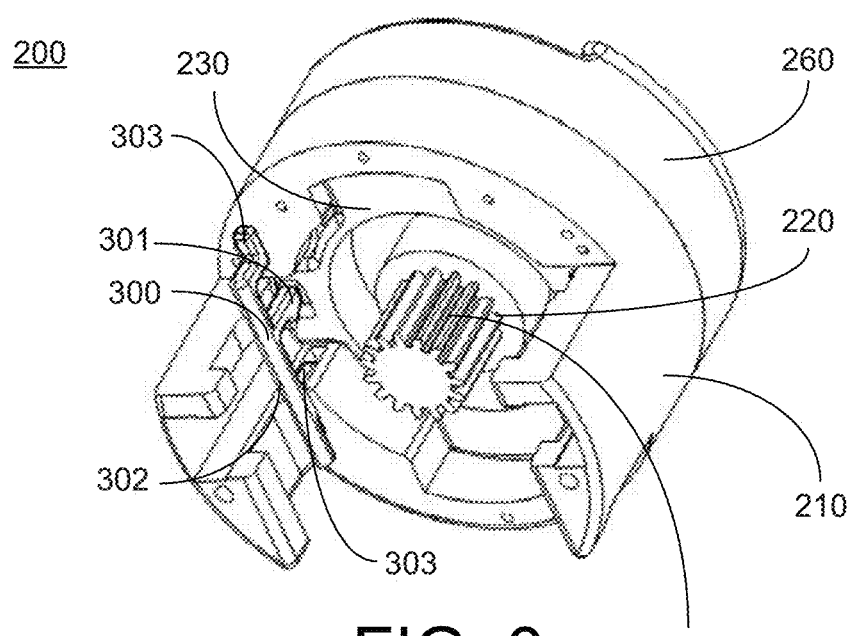
FIG. 8 is a lower perspective view of the trolley of the stethoscope disinfection system of FIG. 1.
Figure 9:
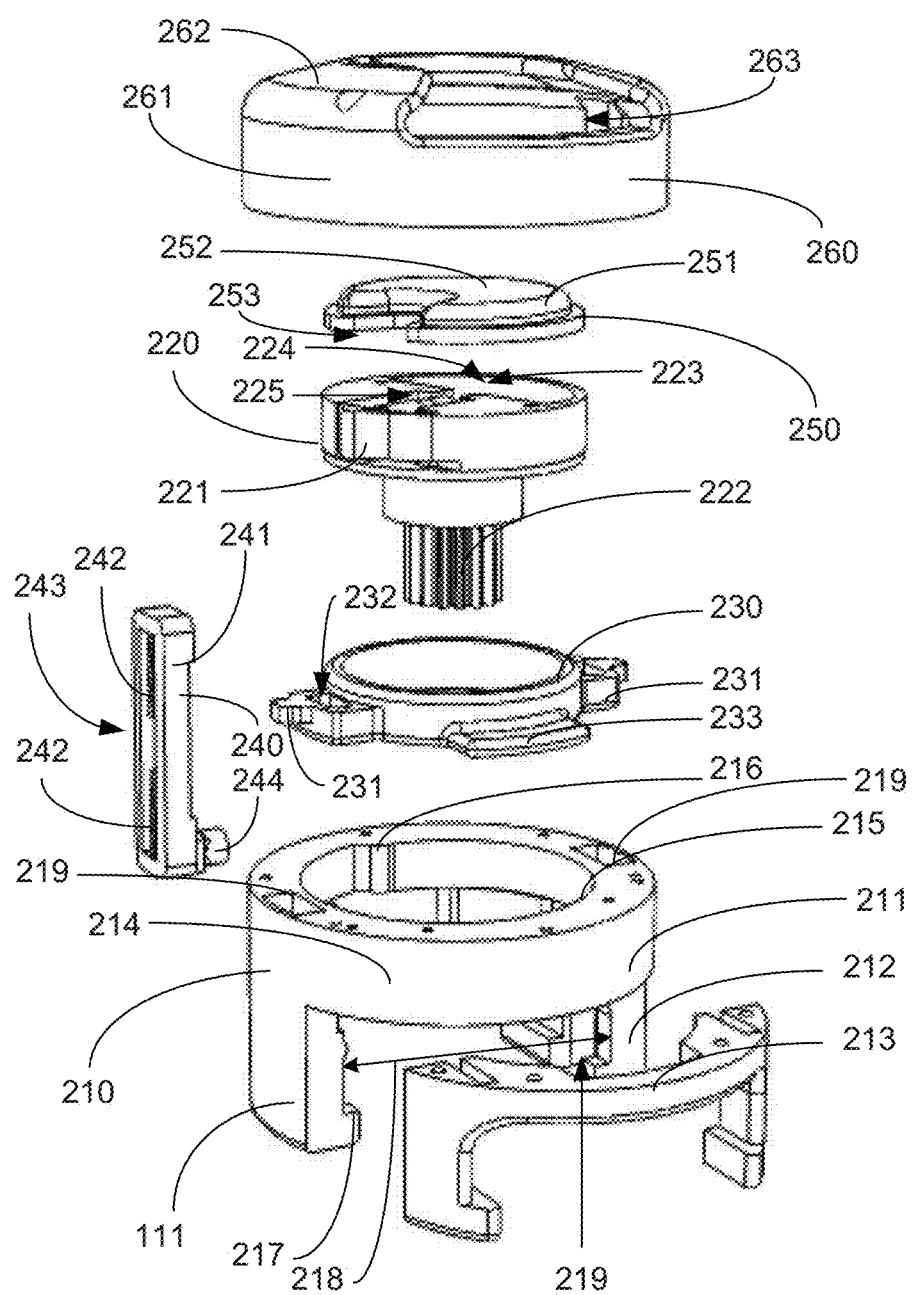
FIG. 9 is a perspective exploded view of the trolley of the stethoscope disinfection system of FIG. 1.

Referring now specifically to FIG. 6, additional aspects of the guide member 100 will now be discussed in greater detail. The guide member 100 may be configured to be attached to a surface of a structure apart from the system 10, including, but not limited to, a wall, a floor, a ceiling, a desk top, a table, a counter top, and the like. Any means or method of attachment known in the art are contemplated and included within the scope of the invention, including, but not limited to, use of fasteners, such as screws, nails, and the like, use of glues or adhesives, magnetic attachment, suction attachment, and the like. Additionally, in some embodiments, the guide member 100 may comprise one or more feet configured to prevent the sliding and/or skidding of the guide member 100 respective to a surface upon which it is placed.

In the present embodiment, the guide member 100 may comprise a plurality of screw holes 170. The screw holes 170 may be configured to cooperate with a screw or nail so as to attach the guide member 100 to a surface. Such attachment may prevent the guide member 100 from moving unintentionally during use.

Additionally, the guide member 100 may further comprise a counter chamber 180. The counter chamber 180 may be configured to permit the positioning therewithin a counter configured to count the number of cycles performed on the guide member 100. Types of cycles includes the number of times a trolley is operated on the guide member 100. The counter may use any mechanical, electrical, or electromagnetic means or method for counting the number of cycles as is known in the art. Furthermore, the counter may be configured to either display the number of cycles or to transmit an indication of the number of cycles to a remote computerized device. In some embodiments, the cycle counter may be comprised by the trolley 200.

Referring now to specifically FIGS. 7-10, the trolley 200 will now be discussed in greater detail. The trolley 200 may comprise a lower housing member 210, a cam member 220, a lock head 230, a spring apparatus 240, a brush member 250, and an upper housing 260.

The lower housing 210 may be configured to facilitate the removable attachment of the trolley 200 to the guide member 100. The lower housing 210 may comprise a body portion 211, one or more guide sections 212, and a removable plate 213.

The body portion 211 may define a generally upper part of the lower housing member 211. The body portion 211 may define an outer wall 214 and an inner wall 215. While any shape is contemplated and included within the scope of the invention, in the present embodiment, the body portion 211 has a generally annular shape, such that the outer wall 214 is generally circular. The inner wall 215 may have an eccentricity, defining an eccentric portion 216. The eccentric portion 216 may be substantially sloped, so as to provide a continuous surface, such that inner wall 215 has a varying radius.

The guide sections 212 may extend generally downward from the body portion 211. Moreover, the guide sections 212 may extend from generally opposing sides of the body portion 211. Additionally, each guide section 212 may comprise a ridge 217 at a lower end thereof. The ridge 217 may be configured to engage with the trolley guide track 150 so as to enable the lower housing member 210, and by extension the trolley 200, to translate along the length of the trolley guide track 150 without disengaging therefrom. Moreover, the engagement between the ridge 217 and the trolley guide track 150 may serve as the attachment between the trolley 200 and the guide member 100. Accordingly, the guide sections 212 may be configured so as to general resist reflection thereof, thereby maintaining engagement with the trolley guide track 150, thereby maintaining attachment between the trolley 200 and the guide member 100.

The guide sections 212 may define therebetween a lower housing aperture 218. The lower housing aperture 218 may be dimensioned so as to permit the body member 110 of the guide member 100 to be positioned therebetween. The lower housing aperture 218 may include openings toward the proximal end and the distal end of the lower housing member 210. This may enable the trolley 200 to translate along the length of the guide member 100 without rubbing the body member 110, thereby enabling the smooth operation of the system 10.

The lower housing member 210 may further comprise one or more spring apparatus chambers 219. The spring apparatus chambers 219 may be formed within the body portion 211 and the guide sections 211. Furthermore, the spring apparatus chambers 219 may be generally open to the lower housing aperture 218, permitting a structure positioned within the spring apparatus chamber 219 to interact with a structure positioned within the lower housing aperture 218. The spring apparatus chamber 219 may be dimensioned so as to permit the spring apparatus 240 to be positioned at least partially therewithin.

The removable plate 213 may be removably attachable to at least one of the body portion 211 and the guide sections 212. The removable plate 213 may be configured to include an aperture corresponding to the lower housing aperture 218, thereby enabling the guide member 100 to pass therethrough. Additionally, the removable plate 213 may be configured to retain the slide guide 300 within the lower housing 210 such that the relative motion between the trolley 200 and the slide guide 300 is substantially limited, but not entirely, as will be discussed in greater detail.

The spring apparatus 240 may be configured to facilitate the transition of various elements of the trolley 200 to differing heights. The spring apparatus 240 may comprise a spring frame 241 and one or more spring members 242 configured to engage with the spring frame 241. The spring apparatus 240 may further comprise a gap 243 between the spring members 242 that is configured to permit a structure of the trolley 200 therewithin to cause the spring apparatus 240 to be in a compressed state, as will be discussed in greater detail hereinbelow. Additionally, the spring frame 241 may comprise an attachment section 244 configured to engage with the spring guide track, as described hereinabove.

The lock head 230 may be configured to be positioned within the lower housing member 210. Additionally, the lock head 230 may be configured to permit at least a portion of the cam member 220 to be positioned at least partially therethrough. Additionally, the lock head 230 may be configured to engage with the cam member 220, enabling the vertical translation of the cam member 220 when the lock head 230 is similarly vertically translated. However, in some embodiments, the engagement between the lock head 230 and the cam member 220 may allow for relative rotation therebetween, such that the cam member 220 may rotate relative to the lock head 230, leaving the lock head 230 motionless from a rotational perspective.

Furthermore, the lock head 230 may comprise one or more arms 231. The arms 231 may be configured to engage with another structure of the trolley 200. More specifically, the arms 231 may be configured to engage with the spring apparatus 240, specifically the spring members 242, thereby enabling the spring apparatus 240 to be transitioned between an expanded state and a compressed state, as will be described in greater detail hereinbelow. In the present embodiments, the arms 231 extend generally outward from opposing sides of the lock head 230. In some embodiments, the arms 231 may comprise an opening 232 configured to permit a portion of the slide guide 300 to be positioned therethrough. Specifically referring to FIG. 8, a head 301 of the slide guide 300 extending from a connecting member 302 thereof may be positionable within the opening 232 of an arm 231. Furthermore, the head 301 may be configured to engage with the arm 231 so as to prevent the relative motion between the lock head 230 and the slide guide 300. Furthermore, the slide guide 300 may comprise one or more slide arms 303 configured to engage with the lower housing member 210 so as to limit the relative motion therebetween, and such that the lower housing member 210 may act as an anchor for the slide guide 300. While the face plate is not shown in FIG. 8, it is understood that the face plate may engage with one of the slide arms 303 as described.

Additionally, the lock head 230 may comprise one or more tabs 233. The tabs 233 may extend in proximal and distal directions. Furthermore, the tabs 233 may be configured to interface with the lower housing member 210 so as to ensure the correct positioning of the lock head 230.

The cam member 220 may be configured to be positioned at least partially within one or each of the lower housing member 210, the lock member 230, and the upper housing member 260. Additionally, the cam member 220 may comprise a depressible arm 221, a rotation section 222, and a dispersing chamber 223.

The depressible arm 221 may be on a generally outer section of the cam member 220. The depressible arm 221 may be configured to engage with another structure of the trolley 200 to be depressed thereby, causing the deflection of the depressible arm 221. More specifically, the cam member 220 may be configured to be positioned such that the depressible arm 221 may engage with the inner surface 215 of the lower housing member 210.

The rotation section 222 may be configured to engage with an element of the guide member 100 so as to impart motion to the rotation section 222, thereby causing the cam member 220 to rotate. More specifically, the rotation section 222 may be configured to interface with the rotation-imparting member 120 of the guide member 100. Yet more specifically, the rotation section 222 may be a toothed device configured to engage with the plurality of teeth 121. When so engaged, the translation of the trolley 200 along the length of the guide member 100 may cause the rotation section 222 to be turned by the stationary plurality of teeth 121, thereby causing the rotation member to turn. Such rotation may cause the cam member 220 to rotate. Any other method of imparting motion to the cam member is contemplated and included within the scope of the invention, including, but not limited to, use of a motor.

The dispersing chamber 223 may be configured to permit a dispersing member to be positioned therewithin. The dispersing chamber 223 may further comprise a reservoir chamber 224 configured to permit a reservoir of a fluid, such as a disinfecting solution, to be positioned therewithin, and a head chamber 225 configured to permit a head of a dispersing member to be positioned therewithin. Furthermore, the head chamber 225 may be positioned generally adjacent to the depressible arm 221, such that the depressible arm 221 partially defines the head chamber 225 and may be deflected into the head chamber 225. Additionally, a channel may be positioned between the reservoir chamber 224 and the head chamber 225 to permit the fluidic communication therebetween, such as permitting tubing to be positioned therewithin.

Figure 10:
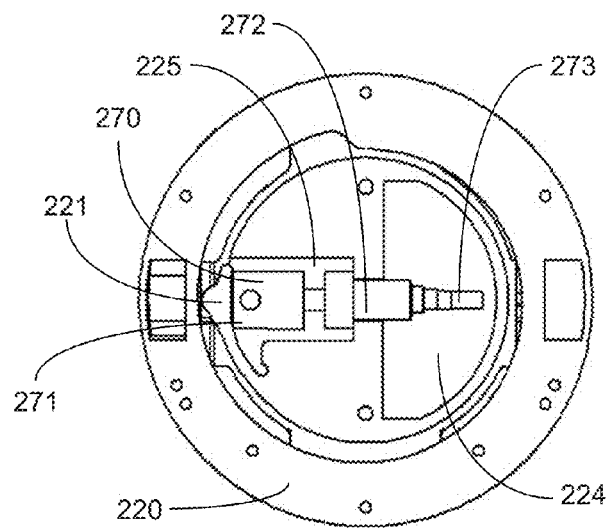
FIG. 10 is a top plan view of a cam member, lock head, and dispersing member of the stethoscope disinfection system of FIG. 1.

Referring now specifically to FIG. 10, additional aspects of the trolley 200 will be discussed in greater detail. The trolley 200 may further comprise a dispersing member 270. The dispersing member 270 may be any device which is operable to disperse a solution, such as a disinfectant solution. In the present embodiment, the dispersing member 270 is pump-action dispersing device, comprising a pump-action head 271, fluidic tubing 272, and a reservoir section 273. In some embodiments, the reservoir section 273 may comprise a reservoir of disinfecting solution. In some embodiments, the reservoir section 273 may be configured to draw from a reservoir of disinfecting solution, with the reservoir being defined by other elements of the trolley 200, such as, for example, the cam member 220, such as the reservoir chamber 224, and the brush member 250. The pump-action head 271 may be configured to, upon being actuated, draw disinfecting solution from the reservoir section 273 through the fluidic tubing 272 and disperse the solution therefrom. The pump-action head 271 may be oriented so as to disperse the disinfecting solution generally upward, which is to say, away from the cam member 220. The pump-action head 271 may be positioned so as to be actuated by another structure of the trolley 200, more specifically, the depressible arm 221. When the depressible arm 221 is deflected into the head chamber 225, it may actuate the pump-action head 271, thereby causing the dispersing of the disinfecting solution.

Referring to FIGS. 1-10, it is contemplated and included within the scope of the invention that, as the trolley 200 translates along the length of the guide member 100, the cam member 220 may be rotated by interaction between the plurality of teeth 121 and the rotation section 222, thereby causing the depressible arm 221 to be deflected inward due to the eccentricity of the inner wall 215. The deflection may cause the depressible arm 221 to actuate the dispersing member 270, causing the dispersion of the disinfecting solution generally upward. Moreover, due to the rotation of the cam member 220, the dispersing member 270 may similarly be rotated. This may cause the dispersing of the disinfecting solution to be performed while the dispersing member 270 is rotating, thereby resulting in a rotated dispersion of the disinfecting solution. This may advantageously result in the disinfecting solution being dispersed while at differing points beneath a portion of a stethoscope head that is positioned within the upper housing member 260, as will be discussed in greater detail hereinbelow. Moreover, due to the stethoscope head not rotating, a more complete application of the disinfecting solution to the stethoscope head is accomplished.

The brush member 250 may be positioned generally above the cam member 220. Furthermore, in some embodiments, the brush member 250 may be attached to and carried by the cam member 220. Additionally, the brush member 250 may be configured so as to be rotated by the cam member 220. The brush member 250 may comprise a body member 251, a brush surface 252, and an aperture 253. The brush surface 252 may be an upper surface of the body member 251. Furthermore, the brush surface 252 may be configured to provide mechanical interaction with a portion of a stethoscope head when rotated, designed to remove, dislodge, or otherwise clean the stethoscope head from any foreign material. Accordingly, the brush surface 250 may comprise any structures, features, or characteristics that are conducive to and facilitate such function, including, but not limited to, bristles, matting, webbing, ridges, grooves, and the like, and may be formed of any material conducive to such purposes. Furthermore, in order to effectively clean the bell of a stethoscope, the brush surface 250 may include structures or features capable of extending at least partially into a bell. Additionally, due to the rotation of the cam member 220, the brush member 250 may be similarly rotated. Such rotation of the brush member 250 while the brush surface 252 is interfaced with a stethoscope head may result in the above-described mechanical interaction. Accordingly, the translation of the trolley 200 may result in the spinning of the brush head 250 to provide mechanical cleaning of a stethoscope head.

The aperture 253 of the brush member 250 may be configured to permit dispersing fluid to be sprayed therethrough. Accordingly, the brush member 250 may be positioned relative to the cam member 220 such that the section of the dispersing member 270 that disperses a disinfecting solution may disperse the fluid through the aperture 253.

The upper housing member 260 may be positioned generally towards the top of the trolley 200 and may comprise a sidewall 261, an upper wall 262, and a stethoscope aperture 263. The stethoscope aperture 263 may be formed in at least one of the sidewall 261 and the upper wall 262. Furthermore, the stethoscope aperture 263 may be configured to permit at least a portion of a stethoscope to be positioned therewithin and retained therein during operation of the system 10. Additionally, the upper housing member 260 may comprise a cavity defined by the sidewall 261 and the upper wall 262, and an opening at the lower end of the sidewall 261, thereby defining a lower end of the upper housing member 260, enabling fluidic communication between the opening, the cavity, and the stethoscope aperture 263. Such fluidic communication may enable the dispersing of the disinfecting solution toward the stethoscope head positioned within the stethoscope aperture 263.

Figure 11:
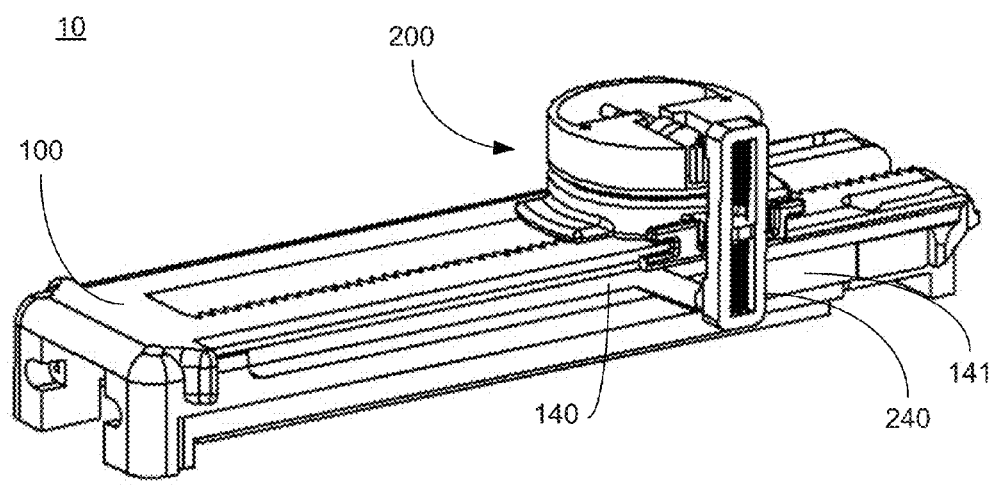
FIG. 11 is a perspective view of the guide member and a partial view of the trolley of the stethoscope disinfection system of FIG. 1 in a first stage of operation

Referring now to FIGS. 11-15, the operation of the stethoscope disinfecting system 10 will now be discussed in greater detail. In FIG. 11, a portion of the trolley 200 is shown in a translated position along the length of the guide member 100 such that the spring apparatus 240 is engaged with the spring guide track 140, specifically, the proximal section 141 of the spring guide track 140. When so positioned, the spring apparatus 240 is at a first elevation and in an expanded state.

Figure 12:
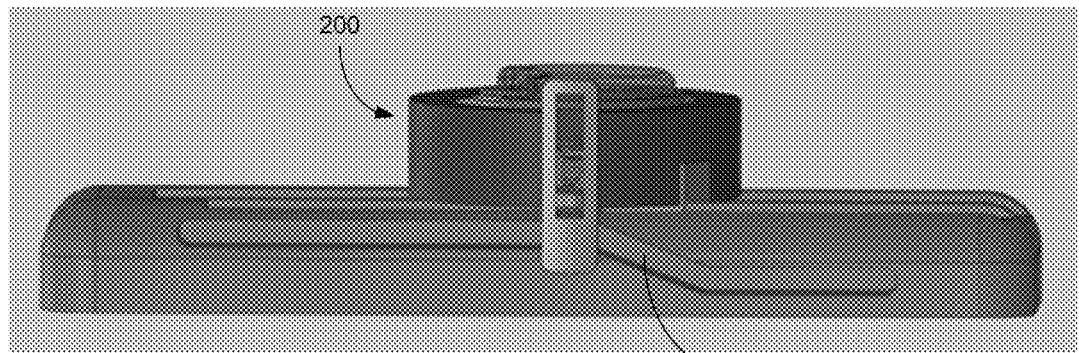
FIG. 12 is a side plan view of the guide member and a partial view of the trolley of the stethoscope disinfection system of FIG. 1 in a stage of operation subsequent to that shown in FIG. 11.

Referring now to FIG. 12, the trolley 200 has been translated in a distal direction through the transition section 143. By transitioning in a distal direction through the transition section 143, the engagement between the slide guide 300 and the arm 231 of the lock head 230, as described hereinabove and shown in FIG. 8, has caused the spring apparatus 240 to be transitioned from the expanded state to a compressed state. Additionally, the spring apparatus 240 has transitioned from the first elevation to the second elevation, with the second elevation being generally higher than the first elevation. The change in elevation, in combination with the interaction between the arm 231 and the slide guide 300, has resulted in the spring apparatus 240 being transitioned to the compressed state.

Figure 13:
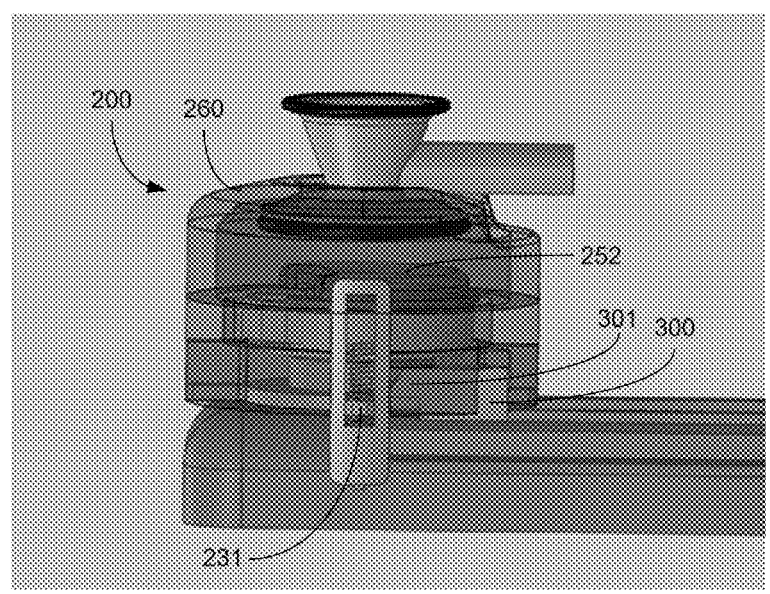
FIG. 13 is a side sectional view of the guide member and trolley of the stethoscope disinfection system of FIG. 1 in a stage of operation subsequent to that shown in FIG. 12.

Referring now to FIG. 13, the trolley 200 has been transitioned to a distal end of the trolley guide track (not shown), more specifically, has been transitioned in a distal direction to a point such that the head 301 of the slide guide 300 has disengaged from the arm 231. This may be enabled by the trolley guide track being configured to enable such translation. It can be seen that the spring apparatus 240 remains in the compressed state. This is for purposes of illustration only, and the maintenance of such a state may be instantaneous and temporary only. Furthermore, it is contemplated and included within the scope of the invention that in the transition between FIGS. 11-13, the disinfecting solution has been dispersed so as to be applied to the stethoscope head as described hereinabove.

Furthermore, it can be seen that a distance exists between the brush surface 252 and a portion of a stethoscope that is shown positioned within the upper housing member 260.

Figure 14:
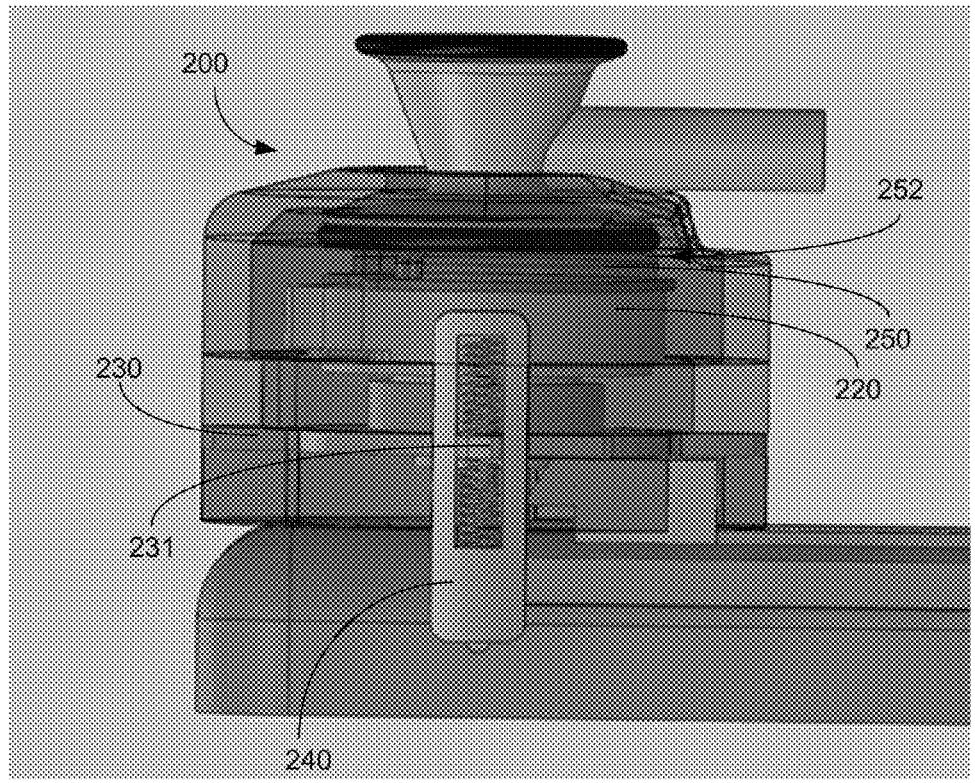
FIG. 14 is a side sectional view of the guide member and trolley of the stethoscope disinfection system of FIG. 1 in a stage of operation subsequent to that shown in FIG. 13.

Referring now to FIG. 14, it can be seen that the spring apparatus 240 has transitioned from the compressed state to the expanded state. Accordingly, due to the engagement between the spring apparatus 240 and the arm 231, and by extension the lock head 230, the lock head 230 may be translated vertically. Accordingly, each of the cam member 220 and the brush head 250 are similarly translated vertically, resulting in the brush surface 252 coming into contact with the stethoscope head. However, the vertical translation of the cam member 220 does not disengage the rotation member 222 from the rotation-imparting member 120 as described hereinabove and shown in FIGS. 3 and 8. Accordingly, as the trolley 200 is translated in a proximal direction, the brush surface 252 may rotate with respect to the stethoscope head, providing mechanical cleaning. This may advantageously remove both foreign contaminants and the disinfecting solution, thereby preventing the formation of and/or removing any biofilm that may exist on the stethoscope head.

Figure 15:
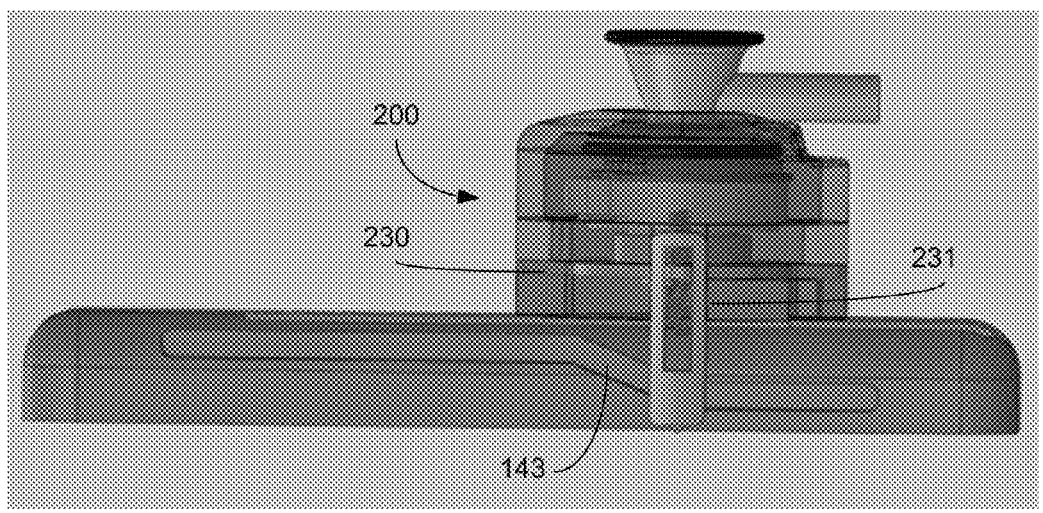
FIG. 15 is a side sectional view of the guide member and trolley of the stethoscope disinfection system of FIG. 1 in a stage of operation subsequent to that shown in FIG. 14.

Referring now to FIG. 15, as the trolley 200 is translated in a proximal direction through the transition section 143, the spring apparatus 240 may transition from the second elevation the first elevation while remaining in the expanded state. Furthermore, the trolley 200 may slide in a proximal direction to a point where the slide guide 300 may re-engage with the arm 231 of the lock head 230, such engagement being described hereinabove. The trolley 200 may be enabled to slide thusly by configuration of the trolley guide track, as described hereinabove.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A stethoscope disinfection system comprising:
   a guide member comprising:
      a body member,
      a rotation-imparting member,
      a slide guide track,
      a spring guide track, and
      a trolley guide track;
   a trolley configured to removably attach to the guide member, the trolley comprising:
      a lower housing member configured to engage with the trolley guide track,
      a cam member configured to engage with the rotation-imparting member to have motion imparted to the cam member thereby, the cam member comprising a dispersing mechanism chamber,
      a lock head comprising an arm,
      a spring apparatus configured to engage with each of the spring guide track and the arm of the lock head, the spring apparatus configured to transition between an expanded state and a compressed state,
      a brush member positioned generally above the cam member and attached to the spring apparatus,
      an upper housing member configured to receive at least a portion of a head of a stethoscope, and
      a dispersing member positioned in the dispersing mechanism chamber; and
   a slide guide configured to engage with each of the arm of the lock head and the slide guide track and to translate along a length of the slide guide track;
   wherein the dispersing member is configured to be actuated by the rotation of the cam member to disperse a disinfectant solution;
   wherein the spring apparatus is configured to transition from the expanded state to the compressed state when translating in a distal direction;
   wherein the spring apparatus is configured to transition from the compressed state to the expanded state upon the slide guide disengaging with the arm of the lock head;
   wherein the brush member is translated vertically by the transition of the spring apparatus from the compressed state to the expanded state;
   wherein the transition of the trolley in a proximal direction causes the brush member to be rotated; and
   wherein the slide guide is configured to engage with the arm of the lock head when the trolley is translated in a proximal direction to a proximal end of the trolley guide track and the slide guide is translated in a proximal direction to a proximal end of the slide guide track.

2. The stethoscope disinfection system of claim 1 wherein the rotation-imparting member comprises a plurality of teeth.

3. The stethoscope disinfection system of claim 2 wherein:
   the body member of the guide member comprises an upper surface including a recess formed therein; and
   the plurality of teeth extend into the recess and are positioned along a length of the recess.

4. The stethoscope disinfection system of claim 2 wherein the cam member further comprises a rotation section configured to engage with the plurality of teeth and have rotation imparted to the cam member thereby.

5. The stethoscope disinfection system of claim 1 wherein:
the spring guide track comprises a proximal section, a distal section, and a transition section;
the spring apparatus is configured to be in the expanded state when engaged with the proximal section of the spring guide track;
the spring apparatus is configured to transition to the compressed state when translating through the transition section in a distal direction; and
the spring apparatus is configured to remain in the expanded state when translating through the transition section in a proximal direction.

6. The stethoscope disinfection system of claim 5 wherein:
the spring apparatus is configured to be at a first elevation when engaged with the proximal section of the spring guide track;
the spring apparatus is configured to transition to a second elevation when translating through the transition section in a distal direction; and
the spring apparatus is configured to transition from the second elevation to the first elevation when translating through the transition section in a proximal direction.

7. The stethoscope disinfection system of claim 1 wherein the lower housing member comprises:
a body portion comprising an exterior wall and an interior wall; and
a pair of guide sections configured to engage with the trolley guide track;
wherein the interior wall comprises an eccentric portion.

8. The stethoscope disinfection system of claim 7 wherein:
the cam member further comprises a depressible arm;
the dispersing member comprises:
a reservoir configured to contain a disinfectant solution, and
a pump-action spray head positioned in fluidic communication with the reservoir;
wherein the depressible arm is configured to interface with and be deflected by the interior wall of the lower housing member when the cam member is rotated;
wherein the deflection of the depressible arm is configured to actuate the pump-action spray head; and
wherein the pump-action spray head is configured to disperse disinfectant solution from the reservoir when actuated by the depressible arm while rotating as a result of the rotation of the cam member.

9. The stethoscope disinfection system of claim 1 wherein the brush member comprises:
a brush surface;
a body member; and
an aperture configured to permit the dispersion of fluid therethrough.

10. The stethoscope disinfection system of claim 1 wherein the upper housing member comprises:
a sidewall;
an upper wall;
a stethoscope aperture formed in at least one of the sidewall and the upper wall configured to receive at least a portion of a head of a stethoscope;
a cavity defined by each of the sidewall and the upper wall; and
an opening at a lower end of the upper housing member.

11. The stethoscope disinfection system of claim 1 wherein at least one of the guide member and the trolley comprises a cycle counter configured to count the number of cycles the trolley performs.

12. The stethoscope disinfection system of claim 1 wherein the guide member is configured to be attached to a surface of an external structure.

13. The stethoscope disinfection system of claim 1 wherein:
the guide member further comprises a tang;
the tang is configured to prevent the detachment of the trolley from the guide member when in an undeflected state; and
the tang is configured to permit the attachment or detachment of the trolley to the guide member when in a deflected state.

14. A stethoscope disinfection system comprising:
a guide member comprising:
a body member comprising:
an upper surface including a recess formed therein,
a proximal end wall, a distal end wall, and
opposing sidewalls,
a rotation-imparting member,
an aperture formed in the proximal end wall,
a slide guide track,
a spring guide track including a proximal section, a distal section, and a transition section, and
a trolley guide track; and
a trolley configured to removably attach to the guide member, the trolley comprising:
a lower housing member comprising:
a body portion comprising an exterior wall and an interior wall, and
a guide section configured to engage with the trolley guide track,
wherein the interior wall comprises an eccentric portion,
a cam member comprising:
a depressible arm,
a rotation section configured to engage with the rotation-imparting member and have rotation imparted to the cam member thereby, and
a dispersing mechanism chamber,
a lock head comprising an arm,
a spring apparatus comprising:
a spring frame configured to engage with the spring guide track, and
a spring member configured to engage with each of the spring frame and the arm of the lock head,
wherein the spring apparatus is transitionable between a compressed state and an expanded state,
a brush member positioned generally above the cam member and attached to the spring apparatus, the brush member comprising a brush surface,
an upper housing member configured to receive at least a portion of a head of a stethoscope,
a dispersing member positioned in the dispersing mechanism chamber, the dispersing member comprising:
a reservoir configured to contain a disinfectant solution, and
a pump-action spray head positioned in fluidic communication with the reservoir; and
a slide guide configured to engage with each of the arm of the lock head and the slide guide track and to slide along a length of the slide guide track;
wherein the cam member is configured to be rotated through the engagement with the rotation imparting member when the trolley is translated proximally or distally when coupled to the slide guide;

wherein the depressible arm is configured to interface with and be deflected by the inner wall of the lower housing member when the cam member is rotated;

wherein the deflection of the depressible arm is configured to actuate the pump-action spray head;

wherein the pump-action spray head is configured to disperse disinfectant solution from the reservoir when actuated by the depressible arm while rotating as a result of the rotation of the cam member;

wherein the spring apparatus is configured to be in the expanded state when engaged with the proximal section of the spring guide;

wherein the spring apparatus is configured to transition to the compressed state when translating through the transition section in a distal direction;

wherein the trolley guide track is configured to enable the trolley to slide distally to a point where the slide guide disengages with the arm of the lock head;

wherein the spring apparatus is configured to transition from the compressed state to the expanded state upon disengagement of the slide guide from the arm of the lock head;

wherein the brush member is translated vertically by the transition of the spring apparatus from the compressed state to the expanded state such that the brush surface may interface with a portion of a stethoscope head positioned within the stethoscope aperture;

wherein the transition of the trolley in a proximal direction causes the brush member to be rotated, thereby causing the brush surface to rotate with respect to the portion of a stethoscope head positioned within the stethoscope aperture;

wherein the spring apparatus is configured to remain in the expanded state when translating through the transition section in a proximal direction; and wherein the trolley guide track is configured to enable the trolley to translate in a proximal direction to a point where the slide guide engages with the arm of the lock head.

15. The stethoscope disinfection system of claim 14 wherein:
the spring apparatus is configured to be at a first election when engaged with the proximal section of the spring guide track;
the spring apparatus is configured to transition to a second elevation when translating through the transition section in a distal direction; and
the spring apparatus is configured to transition from the second elevation to the first elevation when translating through the transition section in a proximal direction.

16. The stethoscope disinfection system of claim 14 wherein:
the rotation-imparting member comprises a plurality of teeth;
the body member of the guide member comprises an upper surface including a recess formed therein; and
the plurality of teeth extend into the recess and are positioned along a length of the recess.

17. The stethoscope disinfection system of claim 14 wherein:
the guide member further comprises a tang;
the tang is configured to prevent the detachment of the trolley from the guide member when in an undeflected state; and
the tang is configured to permit the attachment or detachment of the trolley to the guide member when in a deflected state.

18. The stethoscope disinfection system of claim 14 wherein at least one of the guide member and the trolley comprises a cycle counter configured to count the number of cycles the trolley performs.

19. A stethoscope disinfection system comprising:
a guide member comprising:
a body member comprising:
an upper surface including a recess formed therein,
a proximal end wall,
a distal end wall, and
opposing sidewalls,
a rotation-imparting member comprising plurality of teeth extending into the recess, being positioned along a length of the recess,
an aperture formed in the proximal end wall,
a slide guide track,
a spring guide track including a proximal section, a distal section, and a transition section, and
a trolley guide track; and
a trolley configured to removably attach to the guide member, the trolley comprising:
a lower housing member comprising:
a body portion comprising an exterior wall and an interior wall, and
a pair of guide sections configured to engage with the trolley guide track,
wherein the interior wall comprises an eccentric portion,
a cam member comprising:
a depressible arm,
a rotation section configured to engage with the plurality of teeth and have rotation imparted to the cam member thereby, and
a dispersing mechanism chamber,
a lock head comprising an arm,
a spring apparatus comprising:
a spring frame configured to engage with the spring guide track, and
a spring member configured to engage with each of the spring frame and the arm of the lock head,
wherein the spring apparatus is transitionable between a compressed state and an expanded state,
a brush member positioned generally above the cam member and attached to the spring apparatus, the brush member comprising:
a brush surface,
a body member, and
an aperture configured to permit the dispersion of fluid therethrough,
an upper housing member comprising:
a sidewall,
an upper wall,
a stethoscope aperture configured to receive at least a portion of a head of a stethoscope,
a cavity defined by each of the sidewall and the upper wall, and
an opening at a lower end of the upper housing member, and
a dispersing member positioned in the dispersing mechanism chamber, the dispersing member comprising:
a reservoir configured to contain a disinfectant solution, and
a pump-action spray head positioned in fluidic communication with the reservoir; and a slide guide configured to engage with each of the arm of the lock head and the slide guide track and to slide along a length of the slide guide track;

wherein the cam member is configured to be rotated through the engagement with the plurality of teeth when the trolley is translated proximally or distally when coupled to the slide guide;

wherein the depressible arm is configured to interface with and be deflected by the inner wall of the lower housing member when the cam member is rotated;

wherein the deflection of the depressible arm is configured to actuate the pump-action spray head;

wherein the pump-action spray head is configured to disperse disinfectant solution from the reservoir when actuated by the depressible arm while rotating as a result of the rotation of the cam member;

wherein the spring apparatus is configured to be in the expanded state at a first elevation when engaged with the proximal section of the spring guide;

wherein the spring apparatus is configured to transition to a second elevation and to the compressed state when translating through the transition section in a distal direction;

wherein the trolley guide track is configured to enable the trolley to slide distally to a point where the slide guide disengages with the arm of the lock head;

wherein the spring apparatus is configured to transition from the compressed state to the expanded state upon disengagement of the slide guide from the arm of the lock head;

wherein the brush member is translated vertically by the transition of the spring apparatus from the compressed state to the expanded state such that the brush surface may interface with a portion of a stethoscope head positioned within the stethoscope aperture;

wherein the transition of the trolley in a proximal direction causes the brush member to be rotated, thereby causing the brush surface to rotate with respect to the portion of a stethoscope head positioned within the stethoscope aperture;

wherein the spring apparatus is configured to transition from the second elevation to the first elevation while remaining in the expanded state when translating through the transition section in a proximal direction; and wherein the trolley guide track is configured to enable the trolley to slide in a proximal direction to a point where the slide guide engages with the arm of the lock head.

20. The stethoscope disinfection system of claim 19 wherein:
the guide member further comprises a tang;
the tang is configured to prevent the detachment of the trolley from the guide member when in an undeflected state; and
the tang is configured to permit the attachment or detachment of the trolley to the guide member when in a deflected state.

* * * * *